United States Patent [19]

Burton

[11] Patent Number: 4,769,268

[45] Date of Patent: Sep. 6, 1988

[54] THERMOPLASTIC COMPOSITIONS CONTAINING STABILIZED ANTIMICROBIAL AGENTS

[75] Inventor: Wendel L. Burton, Arden, N.C.

[73] Assignee: BASF Corporation, Williamsburg, Va.

[21] Appl. No.: 87,496

[22] Filed: Aug. 19, 1987

[51] Int. Cl.$^4$ .................... B32B 27/00; D02G 3/00
[52] U.S. Cl. .................................. 428/97; 428/907; 523/122; 524/606
[58] Field of Search ............. 428/97, 85, 92, 907; 8/115.57, 115.58, 115.61, 115.64, 650; 523/122; 524/606

[56] References Cited

U.S. PATENT DOCUMENTS 3,640,928  2/1972  Marayama et al. ............... 260/23
4,624,677  11/1986  Guilbault et al. ................ 8/490
4,624,679  11/1986  McEntee ........................ 8/650
4,643,920  2/1987  McEntee et al. ............. 427/434.6
4,649,079  3/1987  Guilbault et al. ............... 428/375

Primary Examiner—Marion C. McCamish
Attorney, Agent, or Firm—Edward F. Sherer

[57] ABSTRACT

The invention relates to the stabilization of antimicrobial bisphenoxarsine and bisphenarsazine compounds by incorporating with the antimicrobial compounds certain free radical scavengers including inorganic salts that contain transition metal cations, such as cuprous iodide, or organic compounds derived from piperidine, such as [bis(2,2,6,6-teteramethyl-4-piperidinyl) sebacate]. Articles, such as fibers, which contain these stabilized antimicrobial compounds have improved antimicrobial activity compared to articles containing the antimicrobial compound without the stabilizer.

26 Claims, 1 Drawing Sheet

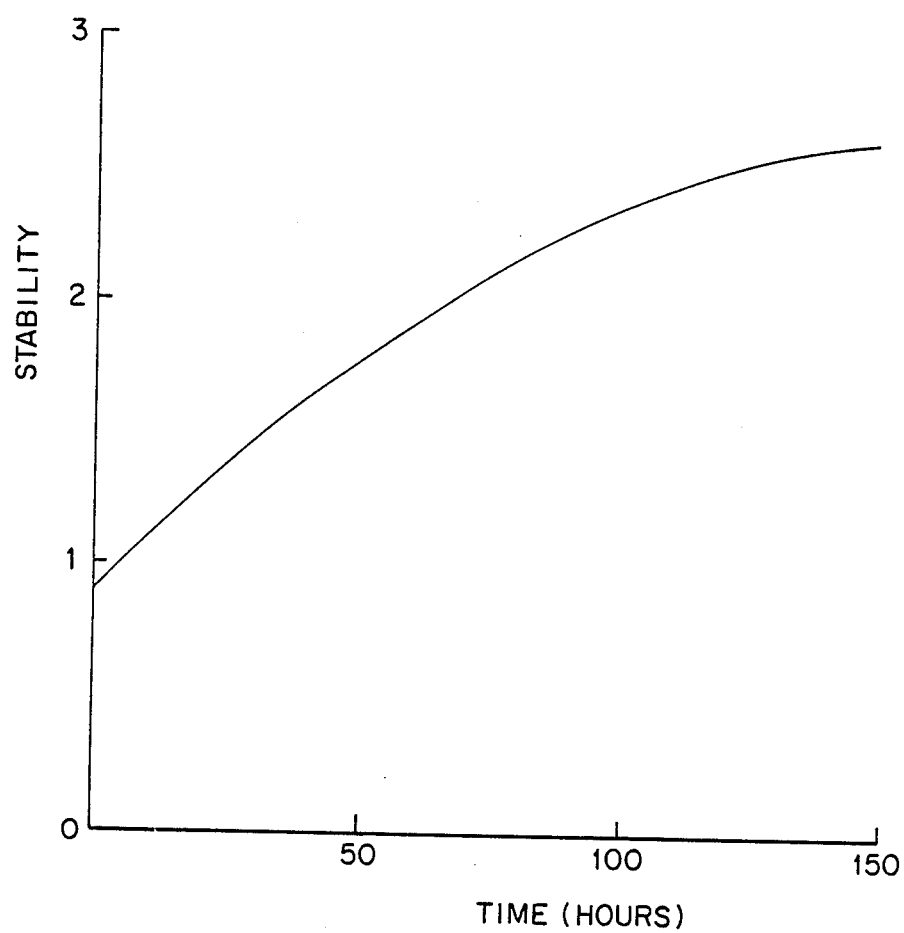
FIGURE

THERMOPLASTIC COMPOSITIONS CONTAINING STABILIZED ANTIMICROBIAL AGENTS

BACKGROUND OF THE INVENTION

A. Field of the Invention

This invention relates to stabilized antimicrobial agents, and more particularly, concerns the stabilization of microbial agents against thermal, oxidative, and/or ultraviolet light degradation and their use in the melt spinning of thermoplastic materials in fiber manufacturing.

B. Description of the Prior Art

Antimicrobial agents are incorporated into thermoplastic fiber materials in order to protect the fiber materials against bacterial attack and to reduce the occurrence of mildew and other undesirable growth on the fiber in its final form, such as carpeting.

During the manufacture of synthetic fiber, the antimicrobial agents of the fiber are exposed to very harsh conditions. For instance, the agents of the fiber are melted with thermoplastic polymers and held at elevated temperatures prior to spinning. During spinning, the agents are subjected to high pressures and are further heated because of friction during their extrusion. Furthermore, the extruded filaments containing the antimicrobial agents are exposed to atmospheric gases during their processing. Because of these harsh conditions, the antimicrobial agents can undergo thermal degradation.

Antimicrobial agents are also subject to oxidative degradation when the agents are exposed to contaminates which cause oxidative degradation. This problem is particularly acute when the contaminate and antimicrobial agents are exposed to moisture and/or heat or are present with the antimicrobial agents at high temperature, i.e., melt-spinning.

Furthermore, antimicrobial agents are subject to deterioration when they are utilized in an outdoor environment or otherwise subjected to ultraviolet light radiation.

As a result of either thermal, oxidative, or ultraviolet light degradation on the antimicrobial agents, the agents lose some or all of their potency. Therefore, large amounts of antimicrobial agents must be included in synthetic articles such as films or fibers to ensure that the article has sufficient resistance to microbial attack.

Thus, there is a need for antimicrobial agents which have increased thermal, oxidative, or ultraviolet stability, and combinations thereof. By the present invention, stabilized antimicrobial agents are provided, as well as articles such as fibers, which contain the stabilized antimicrobial agents.

SUMMARY OF THE INVENTION

It has been surprisingly found that certain antimicrobial agents comprising bisphenoxarsine and bisphenarsazine compounds can be stabilized against degradation caused by heat, ultraviolet light, oxidation, or combinations thereof by incorporating with the compounds certain free radical scavengers. The stabilized antimicrobial agents find particular application during the melt spinning of synthetic polymers to form various articles such as carpets, films, etc.

Articles containing the stabilized antimicrobial agent have an advantage over articles containing unstabilized agents, as lesser amounts of antimicrobial agents are required to achieve the desired level of antimicrobial activity, and antimicrobial activity is maintained in the articles over longer periods of time.

BRIEF DESCRIPTION OF THE DRAWING

The FIGURE illustrates the effectiveness of cuprous iodide as a stabilizer for an antimicrobial agent comprising 10,10'-oxybisphenoxarsine.

DESCRIPTION OF THE PREFERRED EMBODIMENTS

The antimicrobial agents suitable for use in the present invention comprise antimicrobial bisphenoxarsines and bisphenarsazines compounds. Included within these compounds are compounds represented by the following formula:

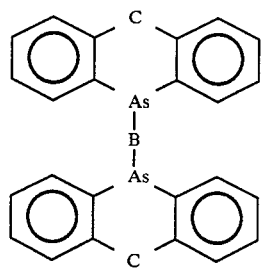

wherein:
C is selected from the group consisting of oxygen and NH; and,
B is selected from the group consisting of oxygen and sulfur.

Examples of bisphenoxarsine and bisphenarsazine compounds include 10,10'-oxybisphenoxarsine (OBPA); 10,10'-oxybisphenarazine; 10,10'-thiobisphenarsazine; 10,10'-thiobisphenoxarsine; and mixtures thereof.

The free radical scavengers suitable for use in the present invention include inorganic compounds containing transition metal cations which are capable of undergoing redox reactions and organic compounds derived from piperidine which are capable of taking on and giving up electrons.

Preferred inorganic compounds include salts that contain transition metal cations which are capable of undergoing redox reactions. These compounds are represented by the following general formula:

$$(M^{+b})_x(A^{-c})_y \qquad \text{I}$$

wherein:
M is a transition metal selected from the group consisting of copper, iron, nickel, cobalt, cerium, and vanadium;
A is an anion of an organic or inorganic acid such as a halide including fluoride, chloride, bromide, and iodide, sulfate, or aliphatic carboxylates; and,
xb=cy.

Suitable copper compounds include cuprous and cupric halides such as cuprous and cupric fluoride, cuprous and cupric chloride, cuprous and cupric bromide, cuprous and cupric iodide, cuprous and cupric sulfate, cupric nitrate, cuprous and cupric salts of organic acids such as cuprous and cupric acetate, and cuprous and cupric formate, and mixtures thereof.

Suitable iron compounds include ferrous and ferric salts of halides such as ferrous and ferric fluoride, ferrous and ferric chloride, ferrous and ferric bromide, ferrous and ferric sulfate, ferrous and ferric nitrate, and ferrous and ferric salts of organic acids such as ferrous and ferric acetate, and ferrous and ferric formate, and mixtures thereof.

Suitable nickel compounds include nickel halides such as nickel fluoride, nickel chloride, nickel bromide, nickel sulfate, nickel nitrate, nickel salts of organic acids as a nickel acetate and nickel formate, and mixtures thereof.

Suitable cobalt compounds include cobaltous halides such as cobaltous fluoride, cobaltous chloride, and cobaltous bromide, cobaltous sulfate, cobaltous nitrate, cobalt salts of organic acids such as cobaltous acetate and cobaltous formate, and mixtures thereof.

Suitable cerium compounds include cerous halides such as cerous fluoride, cerous chloride and cerous bromide, cerous sulfate, cerous nitrate, cerium salts of organic acids such as cerous acetate and cerous formate, and mixtures thereof.

Suitable vanadium compounds include vanadium halides such as vanadium trifluoride, vanadium tetrafluoride, vanadium pentafluoride, vanadium trichloride, vanadium tetrachloride, vanadium pentachloride, vanadium tribromide, vanadium tetrabromide, and vanadium pentabromide, vanadium trisulfate, vanadium trinitrate, vanadium salts of organic acids such as vanadium triformate and vanadium triacetate, and mixtures thereof.

Preferred derivatives of piperidine which are suitable as free radical scavengers include compounds represented by the following formula:

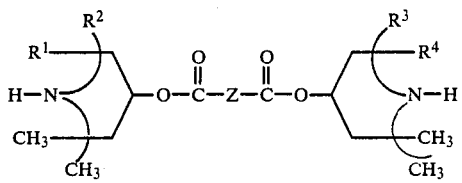

wherein:

R$^1$, R$^2$, R$^3$, and R$^4$ are independently selected from the group consisting of an alkyl having 1 to about 10 carbon atoms, such as methyl, ethyl, isopropyl, pentyl, hexyl, heptyl, and decyl; and, Z is a divalent hydrocarbon, preferably an alkylene group having about 6 to about 12 carbon atoms such as hexylene, heptylene, octylene, nonylene, decylene, undecylene, and dodecylene.

Representative examples of piperidine derivatives (II) include:

[bis(2,2,6,6-tetramethyl-4-piperidinyl)succinate];
[bis(2,2,6,6-tetraethyl-4-piperidinyl)malonate];
[bis(2,2,6,6-tetrapropyl-4-piperidinyl)glutarate];
[bis(2,2,6,6-tetrabutyl-4-piperidinyl)adipate];
[bis(2,2,6,6-tetramethyl-4-piperidinyl)pimelate];
[bis(2,2,6,6-tetrapentyl-4-piperidinyl)suberate];
[bis(2,2-dimethyl-6,6-diethyl-4-piperidinyl)azelate];
[bis(2,2,6,6-tetramethyl-4-piperidinyl)azelate];
[bis(2,2,6,6-tetramethyl-4-piperidinyl)sebacate];
[bis(2,2,6,6-tetramethyl-4-piperidinyl)suberate];
[bis(2,2,6,6-tetramethyl-4-piperidinyl)pimalate];
[bis(2,2,6,6-tetramethyl-4-piperidinyl)adipate];
[bis(2,2,6,6-tetramethyl-4-piperidinyl)glutarate];
bis(2,2,6,6-tetramethyl-4-piperidinyl)malonate];
and mixtures thereof.

The preferred piperidine derivative is [bis(2,2,6,6-tetramethyl-4-piperidinyl)sebacate], TINUVIN 770, which is available from Ciba-Geigy Corporation. The preparation of this compound is carried out by reacting 2,2,6,6-tetramethyl piperidin-4-ol with sebacic acid.

In addition, the free radical scavenger can include a mixture containing one or more piperidine derivatives and one or more inorganic compounds. A particularly preferred mixture comprises cuprous iodide and [bis(2,2,6,6-tetramethyl-4-piperidinyl)sebacate].

Synthetic polymers suitable for use in the present invention include saturated polymers such as polyolefins, e.g., polyethylene and polypropylene, polyvinyl chloride, polyurethane, polyamides such as nylon 6 and nylon 66, polyethylene terephthalate (polyester), polystyrene, styrene-butadiene copolymers, and other elastomers.

The precise manner that the scavenger stabilizes the antimicrobial compound from degradation is not fully understood and need not be. Although the invention is not intended to any particular theory of operation, it is believed the addition of the free radical scavenger to the antimicrobial bisphenoxarsine and bisphenarsazine compounds prevents the oxidation of the trivalent arsenic group to the pentavalent state and thus prevents the conversion of the bisphenoxarsine and bisphenarsazine compounds to phenarsinic acid. Regardless of the theory proposed, it is sufficient to point out that the free radical scavengers operate successfully in the manner disclosed herein.

The amount of free radical scavenger which is necessary for stabilization of the antimicrobial agents will depend on a number of factors, including the antimicrobial agent and free radical scavenger utilized, and thus, there are no set parameters. As a general guideline, the amount of scavenger desired is from about 0.1 to about 25 times by weight of antimicrobial agent utilized. Generally, an amount sufficient to stabilize the antimicrobial agent will be an amount in the range from about 0.01 to about 5.0 weight percent based on the weight of the polymer and antimicrobial agent. More preferably, the amount will be 0.05% to about 1.0% weight percent based on the weight of the polymer and the antimicrobial agent.

The amount of antimicrobial agent included with the synthetic polymer depends on a number of factors including the activity of the agent and the conditions (temperature, time, etc.) of the fabrication. Generally, the antimicrobial agent will be present with the polymer in an amount in the range of from about 0.005% to 2.5% by weight of the polymer and, more preferably, in an amount in the range of from 0.005% to about 0.05% by weight of polymer. Amounts in this range provide sufficient antimicrobial activity to the polymer.

Various methods of including the free radical scavenger and antimicrobial agent in the polymer can be utilized, and are known to persons skilled in the art. In a particularly preferred method, the free radical scavenger, antimicrobial and polymer are melt-processed by heating the ingredients to an elevated temperature, i.e., a temperature sufficient to melt the polymer and allow the polymer to be melt processed, wherein the resulting composition is fabricated in a useful article in various forms such as a film, fiber, sheet, filament, yarn, and other shapes. Nylon 6 is usually melt processed at above 255 degrees Centigrade and nylon 66 is melt processed at above 270 degrees Centigrade. The antimicrobial and free radical scavengers are preferably incorporated in the polymer melt using known machines, such as extruders, kneaders, static mixers and stirrers. In addition, various additives of the type normally used, such as lubricants and mould release agents, nucleating agents, pigments, dyes, reinforcing or non-reinforcing fillers, such as mineral fibres, glass and asbestos fibres, microbeads of glass, talcum, silicon dioxide or mica, antistatic agents, and plasticizers may be added to the polymers.

Compositions specifically contemplated for use herein include polyamides, such as nylon 6 or nylon 66, 10,10'-oxybisphenoxarsine as the antimicrobial compound, and cupric iodide or [bis(2,2,6,6-tetramethyl-4-piperidinyl)sebacate]as the free radical scavenger. Nylon is a particularly desirable application because of its desirable properties as a fiber in a carpet. Preferably, the nylon, 10,10'-oxybisphenoxarsine, and free-radical scavenger are melt-spun into a nylon fiber by extruding nylon, the antimicrobial agent, and the free radical scavenger at a melt temperature of, for example, above 255 degrees Centigrade for nylon 6, through a spinneret to form a number of molten streams and processing the molten streams by standard procedures known to one skilled in the art to converge the formed filaments into yarn. The molten streams are preferably quenched in an inert atmosphere, i.e., an atmosphere substantially free of oxygen such as a nitrogen, steam, or carbon dioxide atmosphere. The yarn finds particular application in carpets. While combining the free radical scavenger with the antimicrobial agent improves the stability of the antimicrobial agent, the resultant distribution of the antimicrobial agent and free radical is unknown; one can assume a random distribution, but it is possible that the scavenger and antimicrobial agent interact.

The invention is further exemplified by the examples below, which are presented to illustrate certain specific embodiments of the invention, but are not intended to be construed so as to be restrictive of the spirit and scope thereof.

EXAMPLE I

The stability of OBPA using cuprous iodide (CuI) as a free radical scavenger in a nylon 6 fiber was compared to the stability of OBPA without any scavenger in nylon.

The tests were carried out by mixing, as chips, an amount of 5,000 ppm of OBPA with the nylon. In test 2, an amount of 1,000 ppm cuprous iodide was mixed with OBPA, and this admixture was mixed with nylon 6. The mixtures were melt extruded to form strands, which, when draw-knitted, yielded 28 filaments at a total denier of 92. Next, the resulting hoselegs were exposed in a Xenon Weatherometer and measured for ppm of undegraded OBPA per exposure time. The amount of undegraded OBPA was measured by Soxhlet extracting a sample with methanol and assaying it by high performance liquid chromatography. The results of these tests are shown in Table I.

TABLE I

| TEST NUMBER | OBPA CONCENTRATION (ppm) WEATHEROMETER TIME (hours) | | |
|---|---|---|---|
| | 0 | 48 | 143 |
| 1 Control - OBPA, No CuI | 3,060 | 840 | 340 |
| 2 OBPA With CuI | 2,740 | 1,500 | 890 |

The results of these tests show the effectiveness of cuprous iodide in stabilizing OBPA against light degradation. A plot of the effectiveness of the scavenger is shown in the FIGURE. Stability was measured by the following ratio:

$$\frac{\text{stabilized } OBPA \text{ (Test 2)}}{\text{unstabilized } OBPA \text{ (Test 1)}}$$

From the FIGURE, it can be seen that over 2.5 times more undegraded OBPA remained after 143 hours when cuprous iodide was utilized when compared to unstabilized OBPA after the same amount of time.

EXAMPLE II

The stability of OBPA in polypropylene fiber using [bis(2,2,6,6-tetramethyl-4-piperidinyl)sebacate](BTMPS) was compared with OBPA in polypropylene fiber without any scavenger. The tests were carried out by mixing an amount of 1,000 ppm of OBPA, polypropylene chips and, in Test 2, 2,500 ppm of BTMPS, melt extruding the mixture to form strands, drawing the strands, and knitting the drawn strands into hoselegs. The hoselegs were then exposed to constant room fluorescent lighting. The amounts, in parts per million, of undegraded OBPA were determined in the same manner as in Example I. The results of these tests are shown in Table II.

TABLE II

| TEST NUMBER | OBPA CONCENTRATION (ppm) LIGHT EXPOSURE TIME (weeks) | | |
|---|---|---|---|
| | 0 (After Extrusion) | 4.0 | 10.0 |
| 1 Control, OBPA, No BTMPS | 520 | 20 | 0 |
| 2 OBPA With BTMPS | 980 | 450 | 160 |

The results of these tests show the effectiveness of BTMPS in stabilizing OBPA against thermal and light degradation.

EXAMPLE III

An amount at a use level of 500 ppm of OBPA, which was included as a concentrate in polystyrene or nylon, was mixed together with nylon 6 chips. In Test 2, an amount of 2,500 ppm of BTMPS was mixed with the OBPA and this admixture was mixed with nylon 6. The mixture was melt extruded into either an air or nitrogen quenching system to form filaments. After drawing and texturing, the filaments comprised typical carpet filaments. Next, the filaments were knitted into hoselegs and exposed to a Xenon Weatherometer. The amounts, in parts per million, of undegraded OBPA were determined in the same manner as in Example I. The results of these tests are shown in Table III.

TABLE III

| Test Number | Stabilizer (ppm) | Polymeric Carrier | Atmosphere | OBPA Concentration (ppm) Time (hours) | | | |
|---|---|---|---|---|---|---|---|
| | | | | After Extrusion | Weatherometer 0 | 30 | Fluor. Light[a] |
| 1 | — | Polystyrene | Air | 175 | 125 | 0 | 46 |
| 2 | 2,500 | Polystyrene | Air | 203 | 130 | 0 | 56 |
| 3 | — | Polystyrene | $N_2$ | — | 280 | 0 | 230 |
| 4 | — | Nylon | $N_2$ | — | 320 | 0 | 290 |

The results of these tests show the effectiveness of BTMPS in reducing the thermal degradation of OBPA even in the presence of polystyrene which promotes a decomposition of OBPA in nylon. Removal of the oxidation potential on melt spinning with a nitrogen atmosphere will increase the stability of OBPA, but will not reduce the susceptibility of OBPA to light degradation.

EXAMPLE IV

An amount of 500 ppm of OBPA was mixed together with caprolactam (nylon 6), and, optionally, stabilizer BTMPS and melt extruded into either air or nitrogen quenching system to form filaments. After drawing and texturing, the filaments comprised typical carpet filaments. The filaments were knitted into hoselegs and exposed to fluorescent light. The amounts, in parts per million, of undegraded OBPA was determined in the same manner as Example I. The results are shown in Table IV.

The amount of stabilization appears to be dependent on the nature of the polymer utilized; the nature and amount of other additives used like delustrants, antistatic agents, colorants, and retardants; extrusion conditions, especially the quenching media; and the exposure conditions, light in particular.

Although certain preferred embodiments of the invention have been herein described for illustrative purposes, it will be appreciated that various modifications and innovations of the procedures recited may be affected without departure from the basic principles which underlie the invention. Changes of this type are therefore deemed to lie within the spirit and scope of the invention except as may be necessarily limited to the amended claims of reasonable equivalents thereof.

What is claimed is:

1. A stabilized antimicrobial agent comprising:

TABLE IV

| | | | | OBPA CONCENTRATION (ppm) | | | | |
|---|---|---|---|---|---|---|---|---|
| | | | | | (A) 3.3 WEEKS FLUORESCENT LIGHT | 3.3 WEEKS DARK | MEASURED TOTAL ARSENIC REPORTED AS IF OBPA FROM (A) | DEGRADATION RATE OF OBPA - ppm/wk. |
| TEST NO. | STABILIZER (ppm) | ATMOSPHERE | THEORETICAL | AFTER TAKE-UP | | | | IN LIGHT | IN DARK |
| 1 | — | $N_2$ | 500 | 315 | 50 | 315 | 430,480 | 25 | 0 |
| 2 | — | Air | 500 | 257 | 0 | 101 | 490,480 | 30 | 18 |
| 3 | 1,000 | Air | 500 | 275 | 35 | 100 | 440,480 | 26 | 19 |
| 4 | 1,000 | $N_2$ | 500 | 322 | 60 | 305 | 430,420 | 24 | 2 |

The results of these tests show that the rate of OBPA decomposition by room fluorescent light is less with OBPA stabilized with BTMPS. In addition, OBPA was less stable when spun into a oxygen-containing environment, and this instability continues in the dark, but does not accelerate or otherwise alter the antimicrobial sensitivity in light.

EXAMPLE V

An antimicrobial agent comprising OBPA, as a 5% by weight concentration in a nylon 6 pellet, was added to nylon 6 in an amount to theoretically afford the nylon 6 filaments produced therefrom 500 ppm of OBPA. Prior to extrusion, certain samples were blended with certain scavengers by either mixing the scavenger in pellet form or tumbling the scavenger in powdered form with the OBPA and nylon. The samples were tested for OBPA concentration at certain time intervals in the manner described in Example I above. Samples remained either in darkness, or under room fluorescent lights, or under a Xenon Weatherometer. The results of these tests are shown in Table V.

(a) a bisphenoxarsine compound or bisphenarsazine compound or mixtures thereof having the formula:

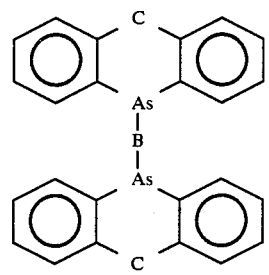

wherein:
C is selected from the group consisting of oxygen and nitrogen; and,
B is selected from the group consisting of oxygen and sulfur; and

TABLE V

| | | | | OBPA CONCENTRATION (ppm) | | | | | | | |
|---|---|---|---|---|---|---|---|---|---|---|---|
| | | AFTER EXTRUSION | AFTER TEXTURING | XENON WEATHEROMETER (hours) | | | UNDER FLUORESCENT LIGHT/DARK (days) | | | | | |
| TEST NUMBER | STABILIZER | | | 40 | 90 | 190 | 18 | 46 | 74 | 116 | 180 | 220 |
| 1 | — | 225 | 150 | 0 | 0 | — | 108/140 | 60/118 | 25/118 | 0/80 | —/70 | —/60 |
| 2 | CuI (250 ppm) | 250 | 220 | 0 | 0 | — | 120/135 | 45/140 | 23/125 | 0/83 | —/70 | —/65 |
| 3 | CuI (250 ppm) BTMPS (2500 ppm) | 335 | 295 | 110 | 50 | 40 | 250/318 | 188/305 | 150/300 | 140/300 | 70/304 | 45/290 |

The results of these tests show the benefit of using the scavengers to provide increased antimicrobially active concentrations from losses due to thermal decay, oxidation induced decay per time (in darkness), and photolytic decay.

(b) a stabilization amount of a free radical scavenger having the formulae:
(i) an inorganic compound capable of undergoing a redox reaction having the formula $$(M^{+b})_x(A^{-c})_y$$

I wherein:
M is a transition metal selected from the group consisting of copper, iron, nickel, cobalt, cerium, and vanadium;
A is an anion of an inorganic or organic salt; and, bx=cy;
(ii) a piperidine derivative having the formula:

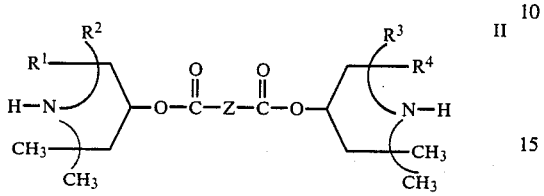

wherein:
$R^1$, $R^2$, $R^3$, and $R^4$ are independently selected from the group consisting of an alkyl having 1 to about 10 carbon atoms; and
Z is a divalent hydrocarbon;
or mixtures of I and II.

2. The stabilized antimicrobial agent recited in claim 1, wherein said bisphenoxarsine or bisphenarsazine compound is selected from the group consisting of 10,10'-oxybisphenoxarsine; 10,10'-oxybisphenarazine; 10,10'-thiobisphenarsazine; 10,10'-thiobisphenoxarsine; and mixtures thereof and said scavenger is present in an amount in the range of from about 0.1 to about 25 times by weight of antimicrobial agent.

3. The stabilized antimicrobial agent recited in claim 2, wherein said free radical scavenger is selected from the group consisting of cuprous halide, cupric halide, cupric acetate, cupric formate, cuprous acetate, cuprous formate, ferrous halide, ferric halide, ferrous sulfate, ferric sulfate, and mixtures thereof.

4. The stabilized antimicrobial agent recited in claim 2, wherein Z is an alkylene group having about 6 to about 12 carbon atoms.

5. The stabilized antimicrobial agent recited in claim 2, wherein said free radical scavenger is a piperidine derivative selected from the group consisting of
[bis(2,2,6,6-tetramethyl-4-piperidinyl)sebacate];
[bis(2,2,6,6-tetramethyl-4-piperidinyl)pimelate];
[bis(2,2,6,6-tetrapentyl-4-piperidinyl)suberate];
[bis(2,2,6,6-tetraethyl-4-piperidinyl)malonate];
[bis(2,2,6,6-tetramethyl-4-piperidinyl)succinate];
[bis(2,2,6,6-tetrabutyl-4-piperidinyl)adipate];
[bis(2,2,6,6-tetrapropyl-4-piperidinyl)glutarate]; and mixtures thereof.

6. The stabilized antimicrobial agent recited in claim 2, wherein said bisphenoxarsine or bisphenarsazine compound is 10,10'-oxybisphenoxarsine and said free radical scavenger is cuprous iodide, [bis(2,2,6,6-tetramethyl-4-piperidinyl)sebacate], or mixtures thereof.

7. The stabilized antimicrobial compound recited in claim 6, wherein said free radical scavenger is cupric iodide.

8. A thermoplastic composition which is resistant to microbial attack comprising:
(a) a synthetic polymer;
(b) an antimicrobial amount of a bisphenoxarsine compound or a bisphenarsazine compound or mixtures thereof having the formula:

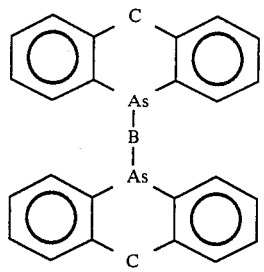

wherein:
C is selected from the group consisting of oxygen and nitrogen; and,
B is selected from the group consisting of oxygen and sulfur; and (c) an amount of a free radical scavenger sufficient to reduce degradation of said bisphenoxarsine compound or bisphenarsazine compound or mixtures thereof having the formulae:
(i) an inorganic compound having the formula $$(M^{+b})_x(A^{-c})_y \qquad \text{I}$$

wherein:
M is a transition metal selected from the group consisting of copper, iron, nickel cobalt, cerium, and vanadium;
A is an anion of an inorganic or organic salt; and, bx=cy;
(ii) a piperidine derivative having the formula:

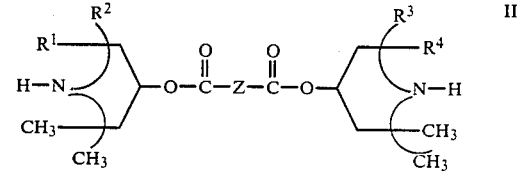

wherein:
$R^1$, $R^2$, $R^3$, and $R^4$ are independently selected from the group consisting of an alkyl having 1 to about 10 carbon atoms; and
Z is a divalent hydrocarbon; or
mixtures of I and II.

9. The thermoplastic composition recited in claim 8, wherein said synthetic polymer is selected from the group consisting of polyolefins, polyamides, polyesters, and mixtures thereof.

10. The thermoplastic composition recited in claim 9, wherein Z is an alkylene group having about 6 to about 12 carbon atoms.

11. The thermoplastic composition recited in claim 10, wherein said free radical scavenger is present in an amount in the range of from about 0.05 to about 1.0 weight percent based on the weight of said polymer and said antimicrobial agent.

12. The thermoplastic composition recited in claim 11, wherein bisphenoxarsine or bisphenarsazine compound is selected from the group consisting of 10,10'-oxybisphenoxarsine; 10,10'-oxybisphenarazine; 10,10'-thiobisphenarsazine; 10,10'-thiobisphenoxarsine; and mixtures thereof.

13. The thermoplastic composition recited in claim 12, wherein said free radical scavenger is a piperidine derivative selected from the group consisting of

[bis(2,2,6,6-tetramethyl-4-piperidinyl)sebacate];
[bis(2,2,6,6-tetramethyl-4-piperidinyl)pimelate];
[bis(2,2,6,6-tetrapentyl-4-piperidinyl)suberate];
[bis(2,2,6,6-tetraethyl-4-piperidinyl)malonate];
[bis(2,2,6,6-tetramethyl-4-piperidinyl)succinate];
[bis(2,2,6,6-tetrabutyl-4-piperidinyl)adipate];
[bis(2,2,6,6-tetrapropyl-4-piperidinyl)glutarate];
and mixtures thereof and an inorganic compound selected from the group consisting of a cuprous halide, a cupric halide, cupric acetate, cupric formate, cuprous acetate, cuprous formate, a ferrous halide, a ferric halide, ferrous sulfate, ferric sulfate, and mixtures thereof.

14. The thermoplastic composition recited in claim 13, wherein said synthetic polymer is nylon 6 or nylon 66, said bisphenoxarsine or bisphenarsazine compound is 10,10'-oxybisphenoxarsine, and said free radical scavenger is [bis(2,2,6,6-tetramethyl-4-piperidinyl)sebacate], cupric iodide, or mixtures thereof.

15. A fiber having resistance to microbial attack comprising the composition recited in claim 14.

16. A carpet having a pile comprising the fibers of claim 15.

17. A method of melt-processing a thermoplastic composition comprising a synthetic polymer and a bisphenoxarsine or a bisphenarsazine antimicrobial compound or mixtures thereof while maintaining the efficacy of said antimicrobial compound comprising:

(A) combining said synthetic polymer and an antimicrobial amount of said bisphenoxarsine or bisphenarsazine compound having the formula:

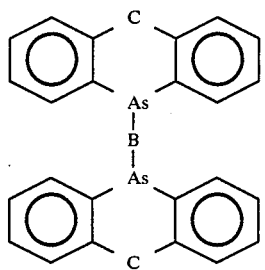

wherein:
C is selected from the group consisting of oxygen and nitrogen; and
B is selected from the group consisting of oxygen and sulfur; and an amount of a free radical scavenger sufficient to reduce degradation of said bisphenoxarsine or bisphenarsazine compound having the formulae:
(i) an inorganic compound having the formula $$(M^{+b})_x(A^{-c})_y \quad \text{I}$$

wherein:
M is a transition metal selected from the group consisting of copper, iron, nickel, cobalt, cerium, and vanadium;
A is an anion of an inorganic or organic salt; and, bx=cy;

(ii) a piperidine derivative having the formula:

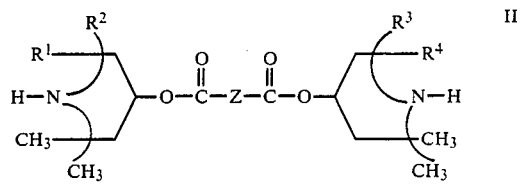

wherein:
$R^1$, $R^2$, $R^3$, and $R^4$ are independently selected from the group consisting of an alkyl having 1 to about 10 carbon atoms; and
Z is a divalent hydrocarbon; or mixtures of I and II; to form a protected antimicrobial thermoplastic composition;

(B) melt processing said protected antimicrobial thermoplastic composition to produce a synthetic article.

18. The method recited in claim 17, wherein Z is an alkylene ground having about 6 to about 12 carbon atoms.

19. The method recited in claim 18, wherein said synthetic polymer is selected from the group consisting of polyolefins, polyamides, polyesters, and mixtures thereof.

20. The method recited in claim 18, wherein said free radical scavenger is present in an amount in the range of from about 0.05 to about 1.0 weight percent based on the weight of said polymer and said antimicrobial agent.

21. The method recited in claim 20, wherein said bisphenoxarsine or bisphenarsazine compound is selected from the group consisting of 10,10'-oxybisphenoxarsine; 10,10'-oxybisphenarazine; 10,10'-thiobisphenarsazine; 10,10'-thiobisphenoxarsine; and mixtures thereof.

22. The method recited in claim 21, wherein said free radical scavenger is a piperidine derivative selected from the group consisting of
[bis(2,2,6,6-tetramethyl-4-piperidinyl)sebacate];
[bis(2,2,6,6-tetramethyl-4-piperidinyl)pimelate];
[bis(2,2,6,6-tetrapentyl-4-piperidinyl)suberate];
[bis(2,2,6,6-tetraethyl-4-piperidinyl)malonate];
[bis(2,2,6,6-tetramethyl-4-piperidinyl)succinate];
[bis(2,2,6,6-tetrabutyl-4-piperidinyl)adipate];
[bis(2,2,6,6-tetrapropyl-4-piperidinyl)glutarate];
and mixtures thereof and an inorganic compound selected from the group consisting of a cuprous halide, a cupric halide, cupric acetate, cupric formate, cuprous acetate, cuprous formate, a ferrous halide, a ferric halide, ferrous sulfate, ferric sulfate, and mixtures thereof.

23. The method recited in claim 22, wherein said synthetic polymer is nylon 6 or nylon 66, said bisphenoxarsine or bisphenarsazine compound is 10,10'-oxybisphenoxarsine, and said free radical scavenger is [bis(2,2,6,6-tetramethyl-4-piperidinyl) sebacate], cuprous iodide, or mixtures thereof.

24. The method recited in claim 23, wherein said thermoplastic polymer is quenched in an inert atmosphere after extrusion of said polymer.

25. A fiber having resistance of microbial attack prepared in accordance with claim 24.

26. A carpet having a pile comprising the fibers of claim 25.

* * * * *